United States Patent [19]

Frankel et al.

[11] 4,015,945
[45] Apr. 5, 1977

[54] DEVICE FOR MIXING BONE CEMENT

[75] Inventors: S. Arthur Frankel, Billings, Mont.;
George E. McGuire, De Pere, Wis.;
Robert O. Wuthrich, Indianapolis, Ind.

[73] Assignee: Zimmer, U.S.A. Inc., Warsaw, Ind.

[22] Filed: Mar. 15, 1976

[21] Appl. No.: 666,728

[52] U.S. Cl. .................... 23/292; 141/65; 220/9 C; 220/17; 98/115 R
[51] Int. Cl.² .......................... B01L 3/00
[58] Field of Search ........... 23/292, 259; 98/115 R; 220/9 C, 17; 141/65; 32/39

[56] References Cited
UNITED STATES PATENTS

| | | | |
|---|---|---|---|
| 1,896,951 | 2/1933 | Hahn | 98/115 R |
| 3,070,275 | 12/1962 | Bostrom | 220/17 X |
| 3,376,583 | 4/1968 | Frey | 98/115 R X |

*Primary Examiner*—Joseph Scovronek
*Assistant Examiner*—Arnold Turk
*Attorney, Agent, or Firm*—Richard H. Brink; David J. Mugford

[57] ABSTRACT

A device for mixing methyl methacrylate monomer and methyl methacrylate polymer to form bone cement in a hospital operating room includes a bowl-shaped container, a replaceable resilient plastic bowl-shaped liner which fits in the bowl-shaped container, a fluid passageway formed between the liner and container and a deflector cap which covers the space between the upper end of the liner and the upper end of the container. Exhaust openings in the side wall of the liner place the interior of the liner in fluid flow communication with the fluid passageway. The methyl methacrylate monomer and polymer are mixed in the bowl-shaped liner. When an exhaust port on the side wall of the container is connected to a vacuum source the ambient atmosphere is drawn through an access opening in the deflector cap towards the interior of the liner to promote aeration of the bone cement reaction mixture and the excess methyl methacrylate monomer vapor admixed with air is evacuated from the mixing device through the exhaust openings, fluid passageway and exhaust port and thereby is prevented from escaping into the operating room.

3 Claims, 6 Drawing Figures

DEVICE FOR MIXING BONE CEMENT

BACKGROUND OF THE INVENTION

This invention relates to a laboratory device for mixing a volatile substance while simultaneously preventing any harmful or obnoxious vapors from escaping into the surrounding environment. Specifically this invention is primarily related to laboratory device for preparing an acrylic bone cement from methylmethacrylate monomer and poly(methylmethacrylate) wherein the components can be manually or mechanically mixed without danger of the monomer vapors escaping into the atmosphere, typically a hospital operating room.

Recently, the Food and Drug Administration approved the use of methyl methacrylate acrylic cement for general clinical use in orthopedic surgery. Since that time bone cement based on methyl methacrylate monomer and poly(methyl methacrylate) has received wide popularity.

The bone cement components are mixed by the surgeon or an assistant in the operating room just prior to use to form a pasty material in a well known manner. The pasty bone cement can then be used for such applications as anchoring prostheses, e.g. femoral hip prostheses in bone.

However, as reported in an article entitled, "Acrylic glue component poses hazard" appearing in JAMA, Nov. 27, 1972, Vol. 222, No. 9 methyl methacrylate monomer "can depress heart and lung function, can cause serious damage to lung tissue, and - in high cencentration - can cause death" when not properly used. These critical problems can be avoided, it is reported, by evaporating excess monomer (monomer not used in the bone cement) by prolonging aeration and mixing time of the cement reactants. The monomer, however, should not be allowed simply to evaporate into the operating area since it has a generally unpleasant odor and can be harmful to the operating room personnel. In addition, the methyl methacrylate monomer is flammable, thus posing another serious problem.

While the mixing can be performed under a hood which is vented to the outside this approach necessitates modification of the existing operating room system and is therefore not satisfactory. It has also been proposed to use a covered mixing bowl which can be connected to the existing operating room vacuum system. However, to date, no entirely satisfactory portable, lightweight, reuseable and inexpensive device has been developed which readily permits for manual mixing and substantially complete aeration of the reactants while simultaneously drawing off harmful or obnoxious vapors and preventing their escape into the operating room.

DISCUSSION OF THE PRIOR ART

Many devices are known for mixing cements, plastics and other types of chemical reactants under vacuum conditions to remove air from the reaction mass and/or to draw off vapors formed during or added to the reaction. Devices of this nature have frequently been used in preparing dental castings and investment molds or other plastic cements and molding materials. Several such devices are described in the following United States Patent Nos. 2,453,914 — Hollenback; 2,696,022 — Steinbock, et al.; 2,777,177 — Steinbock, Jr., et al.; 2,973,187 — Wehmen; 3,343,817 — Carangelo, et al.; and 3,640,510 — Lea. However, none of these mixing devices are satisfactory for mixing the components of acrylic bone cement or other substances which require substantial aeration for curing or otherwise. Moreover, these devices are all closed systems and are not amenable to manual mixing, e.g. kneading by hand.

Of course, almost all chemical laboratories or hospital operating rooms are provided with an exhaust hood which is connected to a low pressure source or exhaust fan which can draw off vapors and gases from the reaction system. However, the use of such hoods is disadvantageous since they are not often convenient to the operating area. Furthermore, there is a substantial risk that the surgeon or assistant will breath in the vapors as they are drawn towards the hood.

It is also known to provide open sinks or vats with evacuating means to prevent any harmful or obnoxious vapors from escaping into the surrounding environment. Two such devices are described in U.S. Pat. Nos. 1,896,951 — Hahn and 3,376,583 — Frey. However, these arrangements are obviously unsuitable for such applications as mixing a bone cement which requires sterility. Furthermore these devices are neither portable or inexpensive and would require substantial modification of the operating room or laboratory. Moreover, no provision is made to assure proper aeration in these devices.

Therefore, the present invention provides a simple, economical, lightweight and portable mixing device for an acrylic bone cement which includes means for connecting to an existing low pressure source, such as a vacuum line or exhaust fan to prevent the harmful methyl methacrylate monomer vapors from escaping into the operating room and also directs ambient air into the mixing area to assure proper aeration of the bone cement.

SUMMARY OF THE INVENTION

The device for mixing acrylic bone cement according to the present invention includes an open bowl-shaped container having an exhaust port in its side wall and a hose barb or other means for connecting the exhaust port to a low pressure source; a replaceable, sterilizeable open bowl-shaped plastic liner which fits within and spaced away from the bowl-shaped container, exhaust openings at the upper end of the side wall of the liner to bring the inside of the liner into fluid flow communication with the space between the liner and container; and a deflector cap which has a first or lower annular disc which fits over the space between the container and liner and rests on a rim at the upper end of the liner and covers or blocks any exhaust openings in the rim of the liner and provides an access opening into the liner and also serves to deflect the ambient air towards the bottom and center of the liner, and a second or upper annular disc which rests on a lip at the upper end of the container, the two discs being connected to the lower and upper edges, respectively of a hollow cylindrical member which also fits snugly within the walls of the container above the liner.

The bowl-shaped container can be formed from any suitable metal or plastic material which will not be adversely affected by the acrylic bone cement components it will come into contact with during use. For increased stability a flat base board can be attached by any suitable means, e.g. solder, cement, bolt, etc., to the bottom surface of the container.

As used herein the term "bowl-shaped" refers to any deep, rounded container, open at its top. Although it would be possible to utilize a container which had straight sides, such as a square or rectangular cross-section, a rounded container and liner is preferred as it makes the mixing operation easier since there will not be any corners or sharp edges. A rounded smooth contoured container without sharp corners or irregularities will also permit a smoother flow pattern of the methyl methacrylate monomer vapors.

The interior of the container is adapted to be evacuated or connected to a low pressure source. This is conveniently accomplished by providing an exhaust port in the side wall and connecting a hose barb or other suitable means over the exhaust port for connecting a line, usually a flexible plastic or rubber hose to a low pressure source, e.g. vacuum line or exhaust fan. The exhaust port is preferably a small round aperture of sufficient diameter to permit connection of the hose barb in a fluid tight manner as is well known in the art. The positioning of the exhaust port on the side wall is not particularly critical and conveniently can be about midway between the bottom and top of the container.

The actual mixing of the reactants is performed in the bowl-shaped liner which can be molded from any suitable resilient plastic material which can be sterilized and which will be inert to the acrylic bone cement reactants and finished product. Since the liner can be made very inexpensively it will usually be discarded after each use. The liner can be sterilized and prepackaged in a sterile wrapper for immediate availability in the operating room.

The bowl-shaped liner will have the same general overall configuration as the bowl-shaped container but will be somewhat shorter in height and smaller in diameter such that the entire liner will fit within the container. To assure that the side and bottom walls of the liner will be spaced away from the walls of the container the liner is provided with spacing means. Preferably, the spacing means take the form of a radially outwardly extending rim around the entire circumference on the upper edge of the side wall of the liner, the rim terminating along its entire length in a skirt member. The diameter of the skirt member should be slightly greater than the diameter of the bowl-shaped container such that the resilient plastic liner can be force fitted into the container with the skirt member maintaining contact with the inside surface of the side wall of the bowl-shaped container while the side walls and bottom of the liner are maintained in a spaced apart relationship from the interior of the container. The rim and skirt will preferably be integrally molded with the bowl-shaped liner. The space between the liner and container forms a fluid passageway through which the methyl methacrylate monomer vapors admixed with air circulate prior to being drawn out of the device through the exhaust port, hose barb and vacuum line.

The side wall at the upper end, i.e. the open end, of the liner is provided with a plurality of exhaust openings, such as in the form of slotted apertures uniformly spaced around the circumference of the liner. Uniform spacing provides for a more even flow distribution of vapors along the inside surface of the liner.

The exhaust openings can extend onto the outwardly extending rim to simplify the molding process. In the preferred embodiment generally rectangular shaped slots will extend a short distance below the upper edge of the liner side wall and over the entire width of the rim member. The skirt member can consist of a plurality of arcuate sections each extending between the slotted openings.

The number and arrangement of the exhaust openings in the side wall of the liner is not particularly critical so long as the total area of the exhaust openings is sufficient to assure a satisfactory flow rate of gases and vapors through the exhaust openings and sufficient outside air being drawn into the interior of the bowl-shaped liner. Care should be taken, however, to limit the extent to which the slotted apertures extend down the side wall since sufficient volume must be provided within the liner to perform the mixing of the bone cement reactants without any of the reactants passing through the slotted apertures. Therefore, it is preferred that the exhaust openings are positioned within the upper one-third to one-fourth, and preferably one-fourth to one-eighth of the side wall of the liner.

Instead of slotted apertures it is possible to have other configurations, such as circular apertures or Y-shaped or T-shaped apertures. It would also be possible to employ a series of horizontally oriented rectangular slots. However the vertically oriented slotted apertures have been found to be particularly suitable.

As previously noted the total area of the exhaust openings should be sufficient to assure adequate flow distribution and ventilation. It has been found that a total exhaust area to provide a flow rate of about 3.5 cubic feet per minute (cfm) or greater with a conventional laboratory or hospital operating room vacuum line will accomplish the dual objectives of preventing harmful or obnoxious vapors from escaping into the surrounding atmosphere and simultaneously drawing in sufficient air to provide adequate aeration of the bone cement mixture.

The deflector cap serves two primary functions. It closes the upper portion of the fluid passageway between the inside surface of the container and outside surface of the liner at the upper end thereof thereby assuring that the ambient air will not be drawn directly into the space between the container and liner. Secondly the deflector cap directs the ambient air drawn into the liner, because of the pressure differential resulting from the connection to the low pressure source, towards the center of the liner where the mixing is taking place. The former function promotes the withdrawal of the vapors inside the liner out through the exhaust openings while the latter function promotes the aeration of the acrylic bone cement reaction mixture.

The deflector cap also functions to help securely seat the bowl-shaped liner in the bowl-shaped container.

The deflector cap can conveniently be formed as an integral unit with a first flat annular disc extending inwardly from the lower edge of a thin hollow cylindrical member and a second flat annular disc extending outwardly from the upper edge of the cylindrical member. There should be a close tolerance between the outside diameter of the cylindrical member and the inside diameter of the bowl-shaped container so that the hollow cylindrical member can be slidably inserted in the container with essentially no air space between the cylinder and the container. The height of the cylindrical member is made sufficient to rest the first or lower annular disc at the upper end or rim of the bowl-shaped liner when the cylindrical member is in its fully inserted position within the container, i.e. when the second or upper annular disc rests on the lip of the bowl-shaped container.

The width, i.e. difference between the outside diameter and inside diameter of the second annular disc is not particularly critical as long as its outer edge extends slightly beyond the edge of the lip of the bowl-shaped container.

The width of the first annular disc must be sufficient to cover the space between the inside surface of the container side wall and the liner. Moreover, in order to accomplish the aeration function the first annular disc must be sufficiently wide so that its central or access opening is completely contained within the circumferential boundary defined by the bowl-shaped liner. That is, the first annular disc extends radially within the bowl-shaped liner. This is accomplished by having the diameter of the access opening less than the inside diameter of the upper end of the liner. Therefore, when the exhaust openings in the bowl-shaped liner take form of slotted openings extending onto the rim member the portion of the slotted openings contained in the rim member will be covered and ambient air will be drawn into the mixing device towards the interior and center of the bowl-shaped liner where the mixing of the acrylic bone cement is being performed.

Since the bone cement is generally mixed by hand the access opening defined by the first or lower annular disc should be made sufficiently wide to permit access into the liner by a human hand. However if mixing is to be performed with a stirring rod, for example, a narrower opening will be sufficient.

The present invention will now be illustrated in greater detail with regard to specific embodiments thereof in connection with the following detailed drawings.

DETAILED DESCRIPTION OF THE INVENTION

Figure 1:
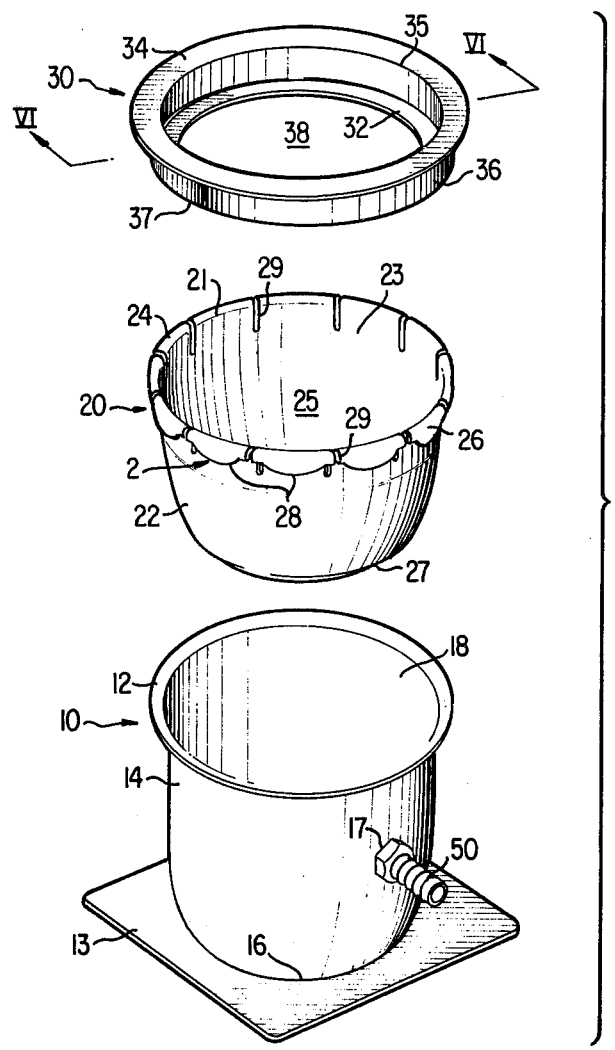
FIG. 1 is an exploded perspective view showing the individual components of the device of the present invention ready for assembly prior to use.

The mixing device of the present invention is indicated generally in FIG. 1 and includes bowl-shaped container 10, bowl-shaped liner 20 and deflector cap 30.

Container 10 is formed from stainless steel and has a lip 12 extending outwardly from its open upper end 18. For extra stability base plate 13 is secured to the undersurface of bottom portion 16 by soldering or any other suitable means.

Figure 2:
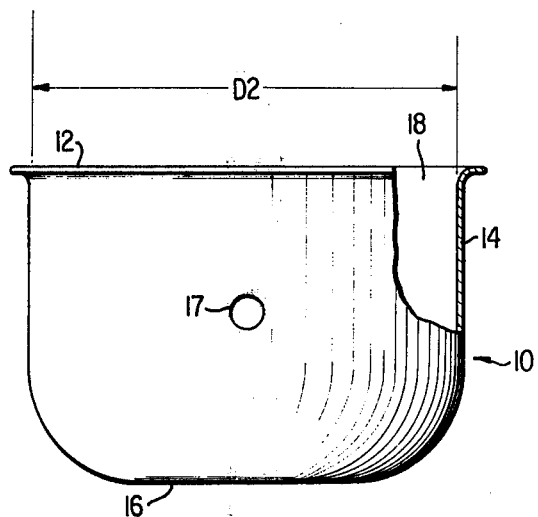
FIG. 2 is a side view showing a partial cross-section of the bowl-shaped container with exhaust port.

An exhaust port 17 (best shown in FIG. 2) is provided in the circumferential side wall 14 of container 10. A hose barb 50 is secured to side wall 14 over the exhaust port 17 in a fluid tight manner by silver soldering or other means well known in the art.

Bowl-shaped liner 20 is molded from polyethylene or any other suitable material which can be sterilized and which will be inert to the methyl methacrylate monomer and other components of the acrylic bone cement. The liner should be resilient so that when circumferential side wall 22 is compressed radially inwardly it will spring back to its original position when the compressive force is released.

Figure 3:
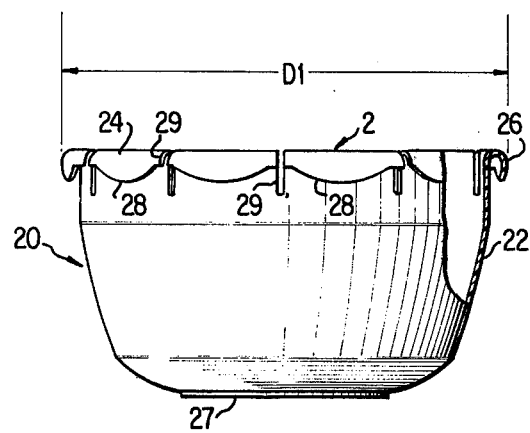
FIG. 3 is a side view showing a partial cross-section of the preferred embodiment of the bowl-shaped liner.

The upper end 23 of liner 20 is provided with spacer means, indicated generally at 2. The spacer means includes rim member 24 which, as seen in FIG. 3 has a generally convex cross-section and extends radially outwardly from the upper edge 21 of side wall 22 and terminates in a skirt member 26 which consists of a plurality of arcuate portions 28. It is apparent that other configurations of the rim and skirt member can be utilized.

Figure 4:
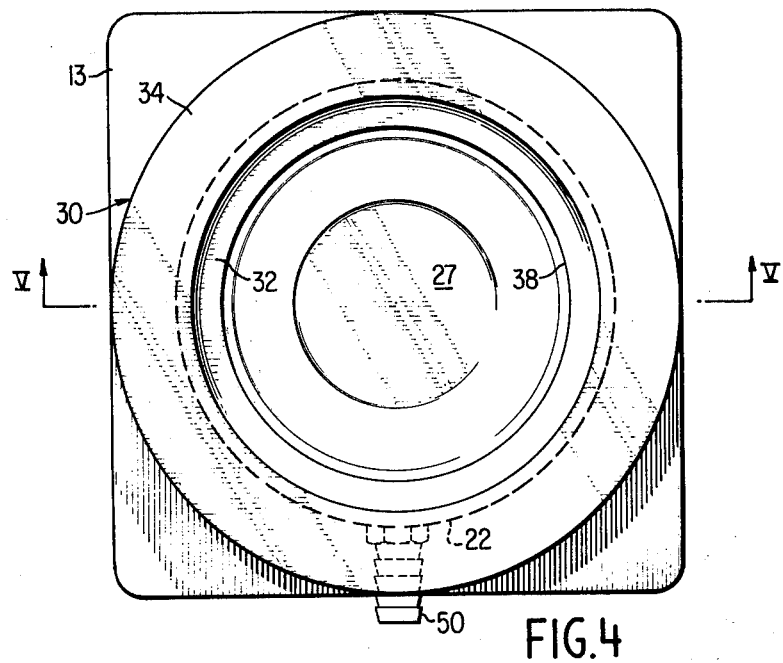
FIG. 4 is a top view of the assembled device of the present invention.
Figure 5:
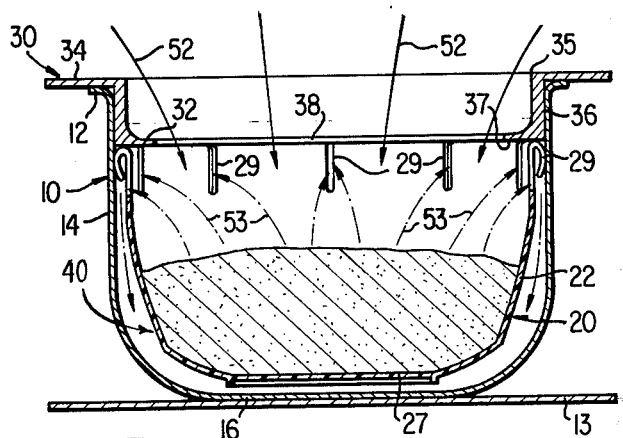
FIG. 5 is a side elevation view, showing a partial cross-section along line V—V of the assembled device of the present invention.
Figure 6:
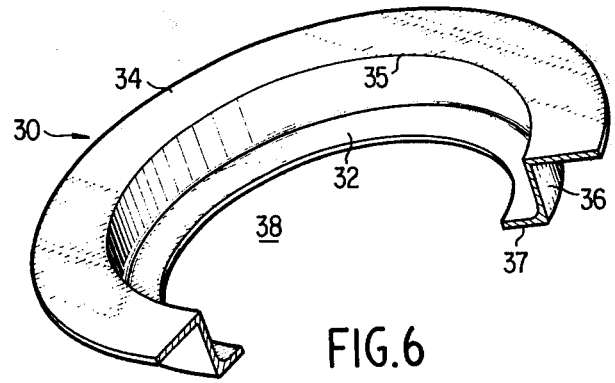
FIG. 6 is a cross-sectional view of the deflector cap taken along line VI—VI.

As seen in FIGS. 4 and 5 the liner 20 fits within container 10 with the side wall 22 and bottom portion 27 of liner 20 spaced apart from the side wall 14 and bottom portion 16 of container 10. The only contact between the liner and container is below upper end 23 by the skirt member 26 of spacer means 2. By making the outside diameter D1 of spacer means 2 slightly larger than the inside diameter D2 of container 10 at its upper end the liner will be held securely in place by virtue of the resiliency of the liner with side wall 22 spaced away from side wall 14. Also, since the height or depth of liner 20 is less than the height or depth of container 10 the bottom portions of the liner and container are also spaced apart from each other. However, it is not critical that the bottom portions remain completely out of contact.

The space between the outer surface of liner 20 and the inner surface of container 10 forms a fluid passageway 40. The fluid passageway is in fluid flow communication with the interior of liner 20 through exhaust openings, shown as slotted apertures 29. The slots extend from a short distance below the upper edge 21 of side wall 22 to the upper edge and over the width of rim member 24. Twelve slots are shown but, of course, a greater or lesser number of slots can be provided so long as sufficient total exhaust opening area is provided to give satisfactory fluid flow rates and flow distribution when the mixing device is in operation.

Deflector ring 30 has lower or first flat annular disc 32, an upper or second flat annular disc 34 and a hollow cylindrical member 36. Disc 34 extends radially outwardly from the upper edge 35 of member 36 while disc 32 extends radially inwardly from lower edge 37 of member 36.

A circular opening or access 38 is defined by the disc 32 and is large enough to permit entry of a human hand. Preferably the opening should have a diameter of at least 3½ inches and more preferably is about 3¾ to 4 inches or greater.

Cylindrical member 36 fits securely within container 10 and over the liner such that the underside of annular disc 32 rests on the rim member 24 of liner 20. When the disc 32 rests on rim member 24 the upper portion of slotted openings 29 in the rim member are covered but the slotted openings in side wall 22 remain uncovered. The diameter of the opening 38 is less than the inside diameter at the upper end of liner 20.

When it is desired to prepare an acrylic bone cement, for example, from methyl methacrylate monomer and methyl methacrylate polymer in a hospital operating room a sterile liner 20 is inserted into the container 10 which as been connected through hose barb 50 in a conventional manner to an external low pressure source (not shown), e.g. the vacuum line usually present in most hospital operating rooms. The reactants, including the methyl methacrylate monomer are placed in the mixing bowl by the doctor, technician or nurse either before or after the deflector cap is put in place within the liner 20 such that the disc 32 covers the slotted openings in rim member 24 and thereby seals the fluid passageway 40. The placement of disc 34 and hollow cylindrical member 36 also helps prevent air from being drawn directly into the fluid passageway 40. In this manner the external low pressure source draws the ambient air towards the central area of the interior 25 of mixing bowl 20 through opening 38 in the direction of arrows 52 thereby promoting the aeration of the bone cement by increasing the oxygen concentration and creating turbulence in the mixing area. Actual mixing of the reactants is usually performed manually. Simultaneously, the methyl methacrylate monomer vapors admixed with air and any other gases or vapors are drawn up along the inside walls 22 of mixing bowl 20 and through the slotted openings 29, as shown by arrows 53, into the fluid passageway 40 and out of the fluid passageway through exhaust port 17 and hose barb 50 to be properly disposed of in a safe and suitable manner.

In order to ensure proper mixing and aeration of the bone cement and removal of vapors through the fluid passageway without escaping into the operating room it has been found that the total area of openings 29 should be sufficient to provide a flow rate of vapors and gases through the openings of at least 3.5 cubic feet per minute (cfm).

After use mixing bowl 20 can be discarded and a new presterilized mixing bowl will be ready for use for the next application.

For most applications it is suitable to provide a replaceable plastic bowl-shaped liner having a total volume of about 20 to 40 cubic inches of which about 60 to about 80% should be available for mixing. The bowl-shaped container will generally have a total volume of about 45 to about 65 cubic inches thereby providing a fluid passageway having a volume, by difference, of about 5 to about 45 cubic inches.

It is, of course, apparent that the mixing device of the present invention can be used to mix any ingredients where it is desired to prevent obnoxious vapors or gases from escaping into the ambient atmosphere while providing ready access to the mixing area and is not limited solely to a bone cement formed from methyl methacrylate monomer and polymer. Similarly other modifications and variations in the parts of the mixing device will be readily apparent to the skilled artisan; For instance, a series of circumferentially spaced lugs on the outside surface of the mixing bowl wall can be provided instead of or in addition to the skirt member to space the liner walls from the container walls.

It shall be understood that the invention is not limited to the specific arrangements shown, and that changes and modifications may be made within the scope of the appended claims.

What is claimed is:

1. A device for mixing a volatile substance which emits an obnoxious or harmful vapor, while simultaneously preventing said obnoxious or harmful vapor from escaping into the ambient atmosphere, said device comprising, A. a bowl-shaped container having an open upper end and an exhaust port in the side wall of said container;
   B. means for connecting said container to a low pressure source, said means associated with said exhaust port;
   C. a replaceable, resilient bowl-shaped plastic liner having an open upper end, said liner fitting entirely within said container; means associated with said liner for spacing the walls of said liner away from the walls of said container, said space defining a fluid passageway; a plurality of exhaust openings uniformly spaced at the upper end of said liner, the interior of said liner being in fluid flow communication with said fluid passageway through said exhaust openings; and,
   D. a deflector cap having
      1. a hollow cylindrical member which is adapted to be slideably positioned within said container,
      2. a first flat annular disc extending radially inwardly from the lower edge of said hollow cylindrical member, said first annular disc being supported at the open upper end of said liner and extending over and closing the space between said container and said liner when said cylindrical member is fully inserted within said container, and
      3. a second flat annular disc extending radially outwardly from the upper edge of said cylindrical member, and said second annular disc being supported at the open upper end of said container when said cylindrical member is fully inserted within said container, said first annular disc defining an access opening into said liner sufficiently large to permit entry of a human hand, the diameter of said access opening being less than the inside diameter of the upper end of said liner, said first annular disc thereby functioning to deflect the ambient atmosphere into the interior and toward the center of said liner when said means (B) is connected to a low pressure source, whereby when a volatile substance is being mixed in said liner the obnoxious or harmful vapor admixed with ambient air will be drawn out of said liner through said exhaust opening into said fluid passageway and out of said device through said exhaust port.

2. The mixing device of claim 1 wherein said means for spacing the walls of said liner away from the walls of said container comprises a rim member extending radially outwardly along the circumference of the upper edge of the side wall of said liner and terminating in a skirt member which has an outside diameter slightly greater than the inside diameter of said bowl-shaped container such that the resilient plastic liner can be force fitted into the bowl-shaped container.

3. The mixing device of claim 2 wherein said exhaust openings comprises a plurality of slotted openings extending a short distance below the upper edge of the side wall of said liner and over the entire width of said rim member, said slotted openings providing a total exhaust opening area sufficient to provide a uniform flow distribution and a fluid flow rate through said openings of at least 3.5 cubic feet per minute.

* * * * *